(12) United States Patent
Elias

(10) Patent No.: US 7,907,988 B2
(45) Date of Patent: Mar. 15, 2011

(54) METHOD AND DEVICE FOR GENERATING A PASSIVE MOVEMENT IN A DIAGNOSTIC DEVICE

(76) Inventor: Ilan Elias, Frankfurt am Main (DE)

( * ) Notice: Subject to any disclaimer, the term of this patent is extended or adjusted under 35 U.S.C. 154(b) by 1018 days.

(21) Appl. No.: 10/375,717

(22) Filed: Feb. 27, 2003

(65) Prior Publication Data

US 2003/0184296 A1    Oct. 2, 2003

(30) Foreign Application Priority Data

Apr. 1, 2002 (DE) ................................. 102 14 798
Apr. 1, 2002 (DE) ................................. 202 05 012 U
Aug. 6, 2002 (DE) ................................. 102 35 963

(51) Int. Cl.
*A61B 5/05* (2006.01)

(52) U.S. Cl. ....................................... 600/415; 600/587

(58) Field of Classification Search .................. 600/415, 600/587
See application file for complete search history.

(56) References Cited

U.S. PATENT DOCUMENTS

| | | | |
|---|---|---|---|
| 5,072,247 A | 12/1991 | Bovee | |
| 5,085,219 A | 2/1992 | Orendahl et al. | |
| 5,099,859 A | 3/1992 | Bell | |
| 5,154,178 A * | 10/1992 | Shah | 600/415 |
| 5,184,074 A * | 2/1993 | Arakawa et al. | 324/309 |
| 5,442,858 A | 8/1995 | Wolters et al. | |
| 5,445,152 A | 8/1995 | Bell et al. | |
| 5,461,314 A * | 10/1995 | Arakawa et al. | 324/318 |
| 5,520,181 A * | 5/1996 | Kreidler et al. | 600/415 |
| 5,533,082 A | 7/1996 | Gronemeyer et al. | |
| 5,541,515 A | 7/1996 | Tsujita | |
| 5,541,516 A | 7/1996 | Rider et al. | |
| 5,577,503 A | 11/1996 | Bonutti | |
| 5,724,970 A | 3/1998 | Votruba et al. | |
| 5,742,136 A | 4/1998 | Ono et al. | |
| 5,743,264 A * | 4/1998 | Bonutti | 600/415 |
| 5,754,046 A | 5/1998 | Busch et al. | |
| 5,772,595 A | 6/1998 | Votruba et al. | |
| 5,851,182 A * | 12/1998 | Sahadevan | 600/407 |
| 5,899,859 A * | 5/1999 | Votruba et al. | 600/415 |
| 5,899,860 A | 5/1999 | Pfeiffer et al. | |

(Continued)

FOREIGN PATENT DOCUMENTS

DE       295 14 603 U1    2/1997

(Continued)

OTHER PUBLICATIONS

Quick et al ("Real-Time MRI of Joint Movement With TrueFISP" -cited by Applicant).*

(Continued)

*Primary Examiner* — Long V Le
*Assistant Examiner* — Ellsworth Weatherby
(74) *Attorney, Agent, or Firm* — Cantor Colburn, LLP

(57) ABSTRACT

A method and an apparatus for generating a passive movement of a patient in a magnetic resonance tomograph. The apparatus includes a support for supporting at least one body part of the patient. The support, together with a patient bed can be moved into a passage of the magnetic resonance tomograph. Driven by a motor, the support can be swiveled about at least one axis inside the passage of the magnetic resonance tomograph. The components of the support and its drive, which are disposed inside the passage of the magnetic resonance tomograph, are made of non-ferromagnetic materials.

36 Claims, 3 Drawing Sheets

U.S. PATENT DOCUMENTS

| | | | |
|---|---|---|---|
| 5,907,664 | A | 5/1999 | Wang et al. |
| 5,931,781 | A | 8/1999 | DeBoer |
| 5,967,980 | A | 10/1999 | Ferre et al. |
| 6,033,415 | A | 3/2000 | Middlestadt et al. |
| 6,138,302 | A | 10/2000 | Sashin et al. |
| 6,411,187 | B1 * | 6/2002 | Rotem et al. ............ 335/296 |
| 6,499,160 | B2 | 12/2002 | Hand et al. |
| 6,499,484 | B1 | 12/2002 | Salminen |
| 6,582,381 | B1 * | 6/2003 | Yehezkeli et al. ............ 601/2 |
| 6,590,391 | B1 | 7/2003 | Shudo et al. |
| 7,221,159 | B2 * | 5/2007 | Griffiths et al. ............ 324/318 |
| 2001/0029330 | A1 | 10/2001 | Nose et al. |
| 2001/0039378 | A1 | 11/2001 | Lampman et al. |
| 2003/0097060 | A1 | 5/2003 | Yanoff et al. |
| 2003/0184296 | A1 | 10/2003 | Elias |

FOREIGN PATENT DOCUMENTS

| | | | |
|---|---|---|---|
| DE | 197 32 784 C1 | | 3/1999 |
| DE | 696 10 176 T2 | | 9/2000 |
| DE | 100 30 507 A1 | | 1/2002 |
| JP | 1-2420506 A | | 9/1989 |
| JP | 3-178638 A | | 8/1991 |
| JP | H04-502387 A | | 4/1992 |
| JP | H10-179542 A | | 7/1998 |
| JP | 2000151175 A | * | 5/2000 |
| WO | WO 00/25692 A1 | | 5/2000 |
| WO | WO 00/28882 A2 | | 5/2000 |
| WO | WO 01/45564 A1 | | 6/2001 |
| WO | WO 03/041057 | | 5/2003 |
| WO | WO 03/0822107 | | 10/2003 |
| WO | WO 2004/004570 | | 1/2004 |

OTHER PUBLICATIONS

Butts K. et al.: "Real-Time MR imaging of joint motion on an open MR imaging scanner", IN; Radiological Society of North America, 83$^{rd}$ Scientific Assembly and Annual Meeting, Chicago, IL 1997, S. 387.

Dietrich et al., Extending the coverage of true volume scans by continuous movement of the subject, 1999 ISMRM Proc., p. 1653.

Johnson et al., "Total-Body MR Imaging in as Little as 18 Seconds", Radiology 202 (Jan. 1997), No. 1, pp. 262-267.

Tacke et al., "Eine Stufenlose pneumatische Beuregungsvorrichtungs fur die dynamische MRT der Halswirbeisauale", Forstr. Rongenser 171 (1999), pp. 249-253.

Quick et al., "Real-Time MRI of Joint Movement with TrueFISP", J. Mag. Res. Imaging, vol. 15, pp. 710-715 (2002); also presented at the 9th Annual meeting of ISMRM, Glasgow, Scotland, Apr. 21-27, 2001, p. 2131.

Muhle et al., "Kinematic CT and MR Imaging of the patellofemoral joint", Eur. Radiol. 9, pp. 508-518 (1999).

Beaulieu et al., "Glenohumeral Relatonships during Physiologic Shoulder Motion and Stress Testing: Initial Experience with Open MR Imaging and Active Imaging-Plane Registration,". Radiology, 1999, vol. 212, No. 3, pp. 699-705.

Shellock, FR et al., editors, Kinematic MRI of the Joints: Functional Anatomy, Kinesiology and Clinical Applications, 2001, CRC Press LLC, Boca Raton, FL.

Quick et al., "Real-Time MRI of Joint Movement with True FISP", Proc. Intl. Soc. Mag. Reson. Med. 9 (2001), p. 2131.

* cited by examiner

METHOD AND DEVICE FOR GENERATING A PASSIVE MOVEMENT IN A DIAGNOSTIC DEVICE

CROSS-REFERENCE TO RELATED APPLICATIONS

This application claims the benefit of a priority under 35 USC 119 (a)-(d) to German Patent Application No. 102 14 798.1 filed Apr. 1, 2002 and German Patent Application No. 202 05 012.2 filed Apr. 1, 2002 and German Patent Application No. 102 35 963.6 filed Aug. 6, 2002, the entire contents of each which are hereby incorporated by reference.

BACKGROUND OF THE INVENTION

Field of the Invention

The present application relates to a method and apparatus for generating a passive movement of a patient in a magnetic resonance tomograph with a support for supporting at least one body part of the patient, which support together with a patient bed or the like can be moved into an imaging passage of the magnetic resonance tomograph.

The Prior Art

To provide for an optimum diagnosis of injuries and disorders of joint, such as an ankle joint it is known to scan a patient of at least relevant body parts by means of a magnetic resonance tomograph (MRT) and to make a diagnosis on the basis of the images obtained. For this purpose, it is frequently required to position or to be able to move the body part concerned in different and defined ways as required. Therefore, apart from static instantaneous images, static images have so far been produced in various joint positions. The joint positions are adjusted manually via a mechanism, and viewing the resulting images is effected by means of an image loop (cine-mode). However, this is particularly time-consuming and therefore can only be applied in individual cases. Thus the possibilities of a modern magnetic resonance tomograph, which also provides for very fast image recordings, are not utilized. Hence, the diagnostics frequently indispensable with a magnetic resonance tomograph, which can excellently represent both the osseous and the cartilaginous parts of the human body as well as its soft-tissue structures, is not being used optimally.

In addition, there is the disadvantage that despite this presently most modern form of diagnosis not all disorders or injuries and damage to the human body can be detected by static instantaneous images, in particular as it has not been possible so far to make images in movement of a sufficient quality. However, this impairs the clinical diagnostics, as thus the probability (sensitivity) to diagnose existing pathological findings with diverse structures is not yet optimally possible or partly not possible. In magnetic resonance tomograph, in contrast to X-ray diagnostics, there have so far not been any firmly predefined and reproducible settings to provide for the representation of real-time movements.

This is in particular due to the fact that as a result of the strong magnetic field in a magnetic resonance tomograph, the use of conventional movement apparatuses is not possible. Conventional electromechanical motors, which are usually employed in movement apparatuses, consist of magnets and coils which in the strong magnetic fields (0.2-3 Tesla) of a magnetic resonance tomograph deflect particularly strongly and thus lead to image distortions, so-called image artefacts. Once such image artefacts occur, however, a proper diagnosis no longer is possible.

BRIEF DESCRIPTION OF THE INVENTION

Therefore, an embodiment of the invention provides a method and an apparatus for a defined reproducible passive movement of a patient in a magnetic resonance tomography without producing image distortions, i.e., image artifacts, which make a diagnosis impossible.

An embodiment of the invention, provides that driven by a motor, the support can be swiveled about at least one axis inside the imaging passage of the magnetic resonance tomograph, and that the components of the support and its drive, which are disposed inside the imaging passage of the magnetic resonance tomograph, are made of non-ferromagnetic materials. Due to this structure, the sensitivity of the magnetic resonance diagnostics with respect to the examination of the joints is increased distinctly. Thus predefined continuous movements can be set and the movements can be reproduced, in order to be able to represent real-time images (online images). The method and apparatus allows a body part to move in the magnetic resonance tomograph within the full scope of movement, passively and as desired for the respective diagnostic situation. Since the diagnostic possibilities have thus been improved and expanded, suspected injuries and the like can be detected and verified far better than has so far been possible. Since the components used in the imaging passage of the magnetic resonance tomography are formed of non-ferromagnetic materials, the occurrence of image artefacts, which make a diagnosis more difficult, is reduced in addition.

In an embodiment the occurrence of image artifacts can furthermore be prevented in that the drive for swiveling the support is effected by means of a piezoelectric motor.

Preferably, the drive for swiveling the support is controlled by a control unit, which is electrically grounded and shielded from magnetic radiation. In the method and apparatus, the movements can therefore be adjusted electronically and automatically controlled from outside the room of the magnetic resonance tomograph in always the same exactly reproducible positions. The position between the body part to be examined and the magnetic resonance tomograph can remain unchanged during the entire diagnostic procedure. At the same time, however, it is for the first time possible to perform precisely defined movements controlled by motors during the imaging procedure. On the one hand, this allows the magnetic resonance tomograph operator to specifically take a certain image, and on the other hand to represent the movement itself in the sense of a real-time image. Beside the use of a piezoelectric motor for driving the support, it is also possible to use pneumatic or hydraulic drives for this purpose.

When the control unit is disposed outside the zone around the magnetic resonance tomograph, in which in operation the magnetic flux density is $\geq 0.2$ Tesla, the function of the control unit is not impaired by the strong magnetic field of the magnetic resonance tomograph. At the same time, image artefacts caused by the control unit can be avoided.

The control of the support can further be improved in that the control unit is provided with at least one sensor, in particular with an optical encoder, for detecting the position of the support or of the motors.

To be able to avoid the occurrence of image artifacts, which make diagnosis more difficult, even more effectively, the control unit can be connected with the drive of the support and possibly with the sensors via electrically grounded and shielded lines, which outside the imaging passage of the magnetic resonance tomograph are provided with ferrites.

In accordance with another embodiment of the invention, the support when driven by a motor, can independently be swivelled about two axes. Thus, the physiological movements of the body parts to be examined can be represented even better.

The physiological movement of an ankle joint can be imitated particularly well with the apparatus when the support can be swiveled about a first horizontal axis and a second axis inclined with respect to the vertical by about 35° in the horizontal plane and by about 18° in the sagittal plane. This inclination of the second axis corresponds to the average geometrical axis of the lower ankle joint as determined by Van den Bogard.

The pressure forces acting on the ankle joint, etc, for instance when running, can be imitated during the examination in the magnetic resonance tomograph in that there are provided means for fixing the at least one body part of the patient on the support, and that at least portions of the support can be moved relative to the fixing means. Preferably, the support can be moved pneumatically or hydraulically relative to the means for fixing the body part. In this way, a stepwise compression of the body part to be examined can occur, which likewise leads to a change in the configuration of the individual parts of the body, which imitate the loads acting for instance when running or the like.

BRIEF DESCRIPTION OF THE DRAWINGS

Other features of an embodiment of the present invention will become apparent from the following detailed description considered in connection with the accompanying drawings that disclose several embodiments of the invention. It should be understood, however, that the drawings are for the purpose of illustration only and not as a definition of the scope and extant of the invention as disclosed and claimed.

In the following an embodiment of the invention will be described in detail by means of embodiments and with reference to the attached drawings, in which.

DETAILED DESCRIPTION OF DISCLOSED EMBODIMENTS

Figure 1:
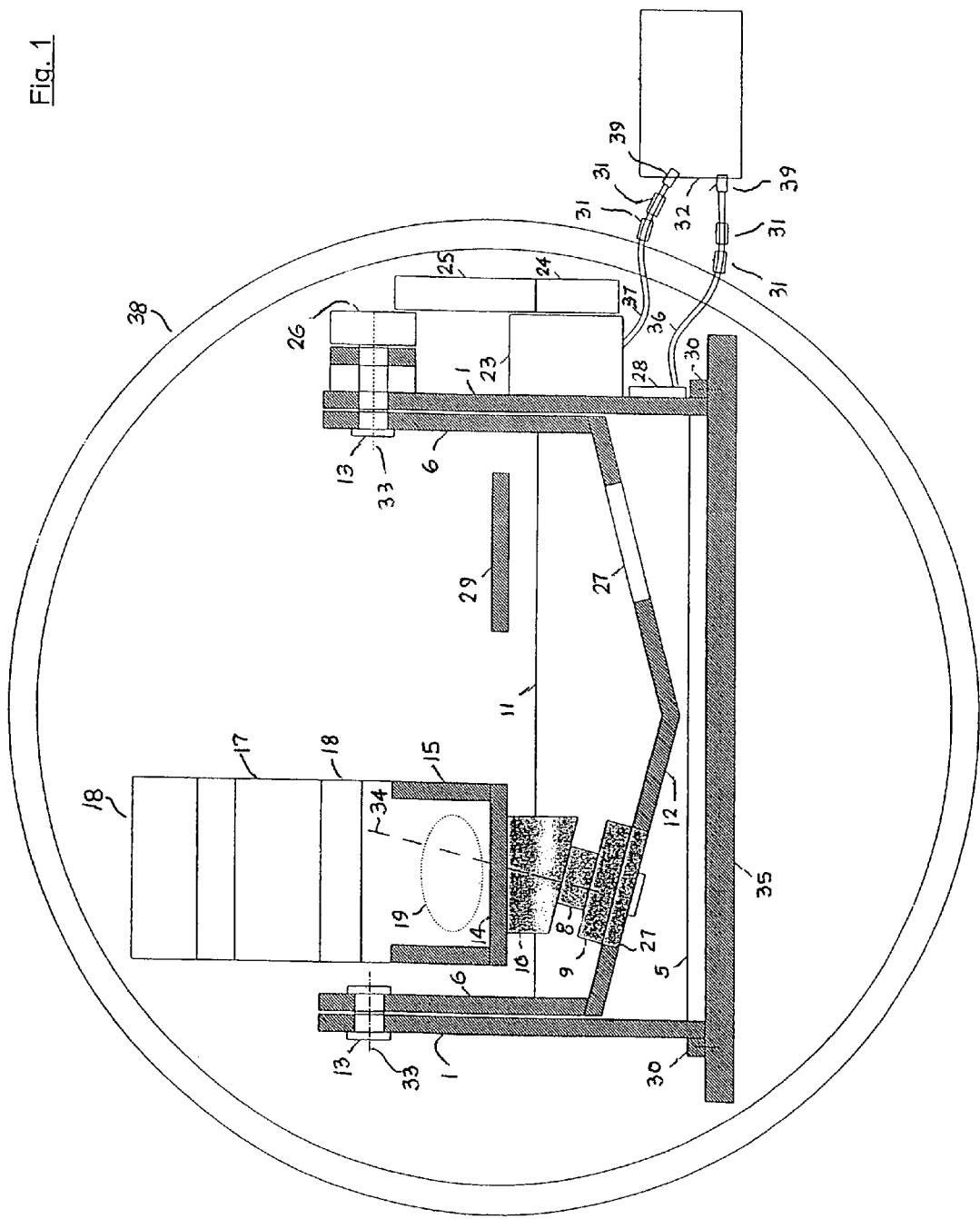
FIG. 1 shows a longitudinal section through an imaging passage of a magnetic resonance tomograph with an apparatus arranged on a patient bed.

The apparatus represented in the drawings is provided for use in a magnetic resonance tomograph (MRT) for instance with a magnetic flux density between 0.2 and 3.0 Tesla. The magnetic resonance tomograph is indicated in FIG. 1 by an imaging passage 38. In the illustrated embodiment, the apparatus is arranged for examining or imaging the ankle joint. The apparatus has a support 14 for the heel of the foot and a support 17 for the sole of the foot disposed at an angle. The inner and outer malleoli of the foot are stabilized by side walls 15, whereas the support 17 for the sole of the foot is retained on a rear wall 16. In FIG. 1, the foot to be examined is indicated schematically by the reference numeral 19.

Figure 2:
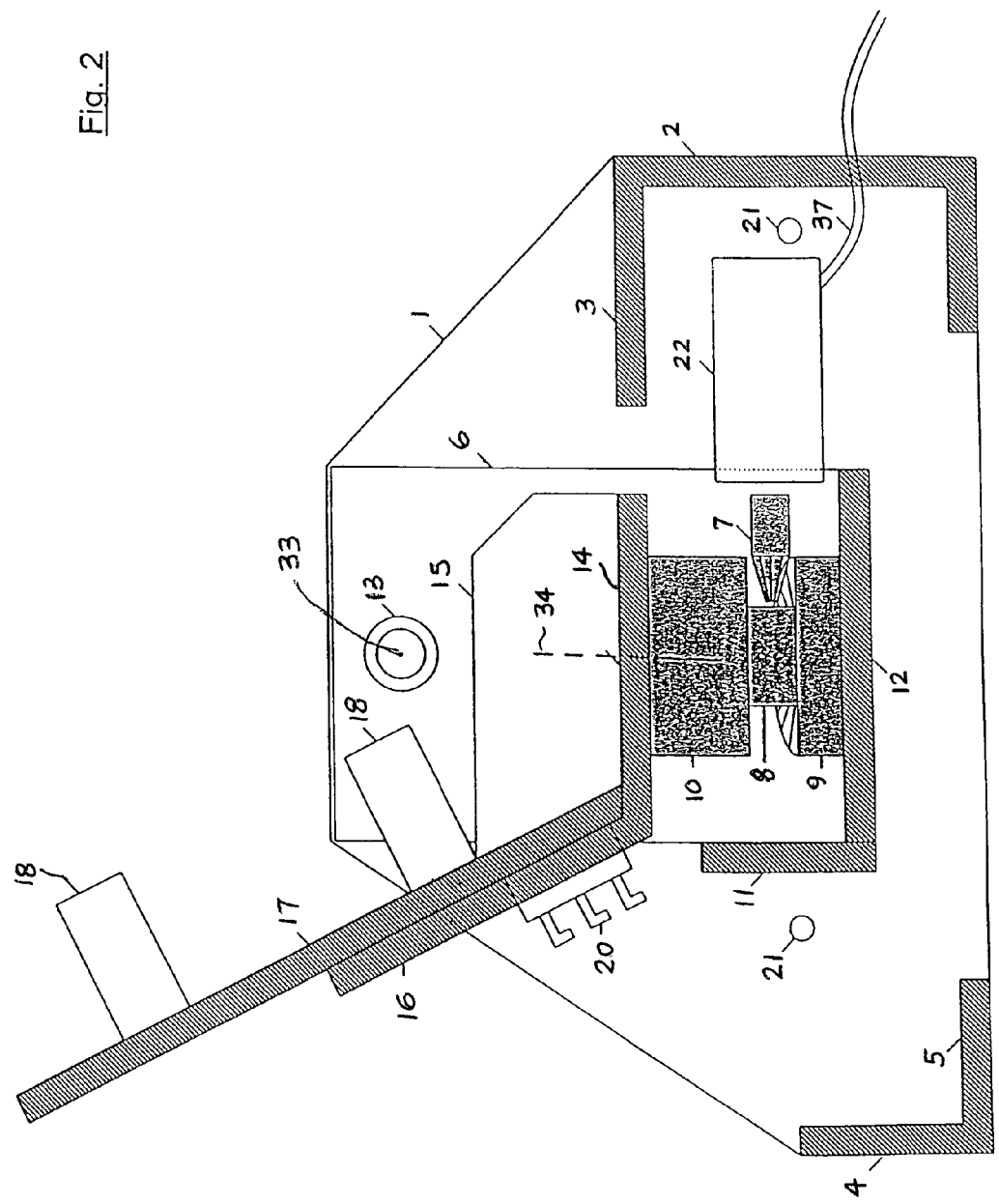
FIG. 2 shows a sectional view of the apparatus vertical to the sectional plane of FIG. 1.
Figure 3:
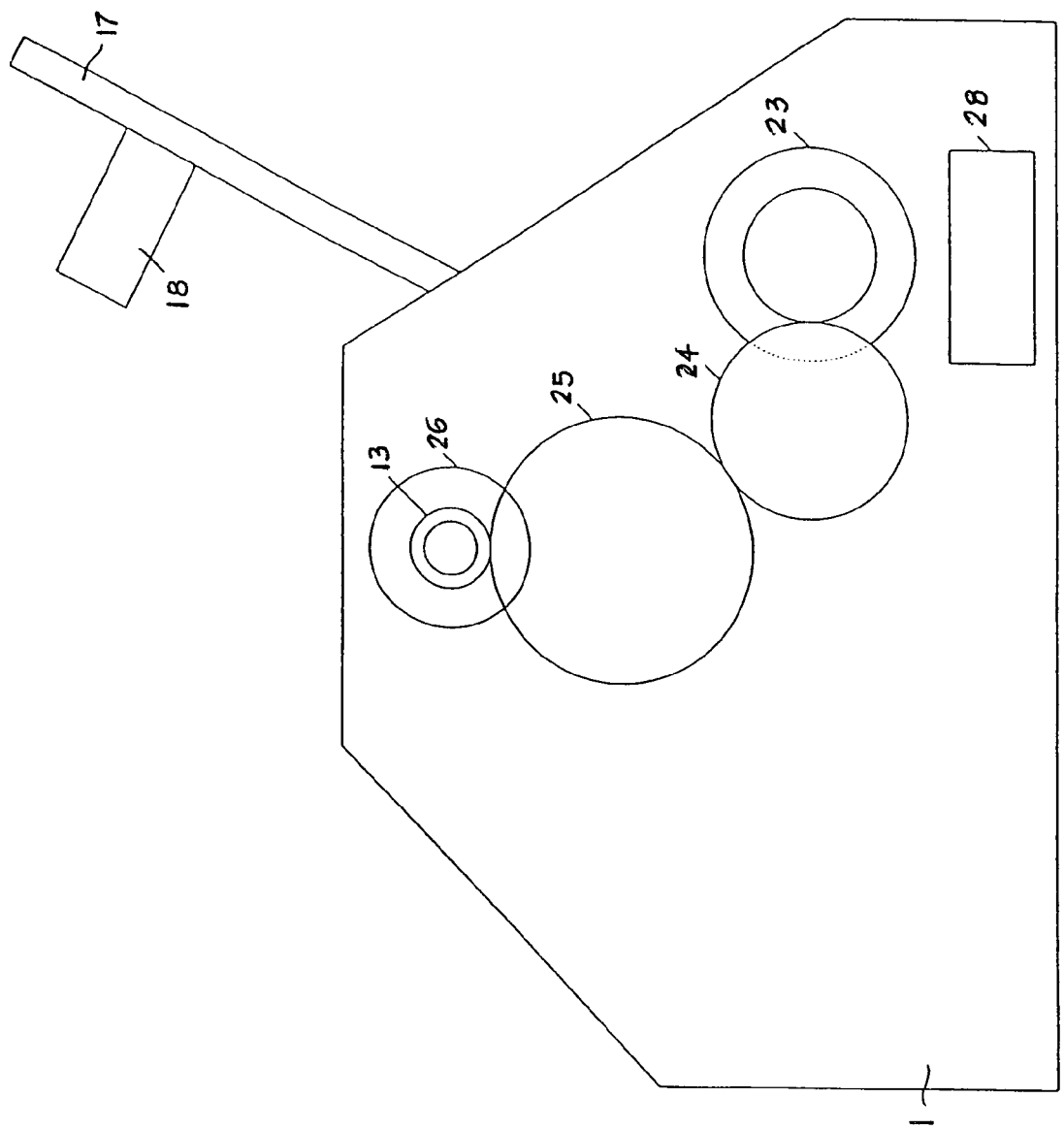
FIG. 3 shows a side view of the apparatus as shown in FIG. 2.

As shown in FIGS. 1 and 2, the apparatus is mounted on a patient bed 35 by means of a connecting unit 30. Together with the patient bed 35, a patient lying on his or her back can be moved into the image passage 38 of the magnetic resonance tomograph, the apparatus being disposed at one end of the patient bed 35. By means of buckles 18, the foot can be maintained fixed in the apparatus. The foot not to be examined can be placed on another support 29 and is not detected in the examination or imaging.

The apparatus disposed on the patient bed 35 furthermore comprises two vertical side walls 1 and a vertical front wall 2 which merges into a horizontal front wall 3. On the side opposite the vertical front wall 2 a vertical rear wall 4 is provided, which is connected with a lower horizontal rear wall 5. Parallel, to the side walls 1 another vertical wall 6 extends, which by means of ball bearings 13 is articulated to the side walls 1 so as to be swivelled about a horizontal axis 33. The vertical walls 6 are connected with each other by a rear wall 11 and a V-shaped bottom wall 12.

In the V-shaped bottom wall 12, two recesses 27 are provided, which can receive a fastening unit 9. Via an intermediate part 8, the fastening unit 9 carries another fastening unit 10 with a gearwheel, on which there is mounted the support 14 for the heel as well as the rear wall 16 with the support 17 for the sole of the foot. The support 14 for the heel as well as the rear wall 16 with the support 17 for the sole of the foot can be rotated relative to the fastening unit 9 via the fastening unit 10. Due to the inclination of the V-shaped bottom wall 12 and the corresponding configuration of the fastening units 9 and 10, the support 14 for the heel with the rear wall 16 and the support 17 for the sole of the foot can be rotated about an axis 34 inclined with respect to the vertical by about 35° in the horizontal plane and by about 18° in the sagittal plane.

The fastening units 9 and 10 have associated thereto a piezoelectric motor 22, which carries a gearwheel 7 with conical tip for moving the fastening unit 10 relative to the fastening unit 9. Similarly, a piezoelectric motor 23 is provided at the vertical side wall 1, which carries a first gearwheel 24 which via another gearwheel 25 can be brought in engagement with a gearwheel 26, which is non-rotatably connected with one of the side walls 6. Driven by the motor 23, the side walls 6 can thus be swivelled relative to the side walls 1.

At the rear wall 16, a pressure valve unit 20 is disposed, by means of which the support 17 for the sole of the foot can be moved relative to the rear wall 16. There can thus be produced a continuously variable pressure acting on the sole of the foot.

In one of the side walls 1, two optical encoders 21 are positioned, which can detect the position of the side walls 6 relative to the side walls 1. Via lines not represented here, the data determined by the encoders 21 can be transferred to an electrobox 28, which in turn is connected with a control unit 32 via a shielded cable 36.

The control unit 32 also actuates the motors 22 and 23 via shielded cables 37. Outside the imaging passage 38 of the magnetic resonance tomograph, ferrite cores 31 are disposed on the shielded lines 36 and 37. The connection of the lines 36 and 37 with the control unit 32 is effected via likewise shielded cable connectors 39.

The materials used for the apparatus are not influenced by the magnetic field of the magnetic resonance tomograph. Therefore they produce no image artefacts that make a diagnosis impossible when non-ferromagnetic materials are used for the components disposed inside the imaging passage 38 of the magnetic resonance tomograph. Such non-ferromagnetic materials include for instance VA4 stainless steel screws and threads, aluminum plates, pins, screws and air-pressure nozzles made of brass, plastic screws, and glass and ceramic ball bearings. The use of semifinished products made of polyoxymethylene (POM) is particularly favorable, as this plastic material absorbs the radiofrequency field (RF) and therefore generates no disturbing radiation.

The illustrated embodiment of the apparatus for generating a passive movement is particularly arranged for the examination or imaging of ankle joints. By means of the motors 22 and 23, the support 14 for the heel as well as the support 17 for the sole of the foot, which is connected with the rear wall 16, can be rotated such that the physiological movement of the ankle joint is imitated. By moving the support 17 for the sole of the foot relative to the rear wall 16 by means of the pressure valve unit 20, a weight load of the foot can be imitated in addition. It is thus possible to make both kinematic and static images from different positions inside the imaging passage 38 of the magnetic resonance tomograph for research and clinical routine diagnosis. As a result, these real-time images of the movements considerably expand the possibilities for using a magnetic resonance tomograph known per se.

Accordingly, while an embodiment of the present invention have been shown and described, it is to be understood that many changes and modifications may be made thereunto without departing from the spirit and scope of the invention as defined in the appended claims.

What is claimed is:

1. A method of acquiring images of a passive movement of a body or at least one part of a body of an object to be imaged in a magnetic resonance tomograph comprising:
   fixing the body or the at least one part of a body on a support to be disposed in an imaging passage of the magnetic resonance tomograph;
   generating a defined reproducible passive movement about two independent axes of the body or the at least one part of a body or the support by a non-ferromagnetic motorized drive for the support while disposing the support and the drive and the body or the at least one part of a body within the imaging passage of the magnetic resonance tomograph; and
   acquiring a series of images continuously in real time during imaging while or during the passive movement of the body or the at least one part of a body or the support.

2. The method according to claim 1 comprising providing shielding against magnetic flux artifacts in the acquired images or the images as acquired.

3. The method according to claim 1 wherein the passive movement comprises applying pressure to the body or the at least one part of a body or the support.

4. The method according to claim 3 wherein the applied pressure is selected from the group consisting of continuous, constant, adjustable, step-by-step, variable, and a combination thereof.

5. The method according to claim 1 wherein the passive movement comprises applying a load on the body or the at least one part of a body or the support.

6. The method according to claim 1 wherein the passive movement imitates a physiological movement of the body or the at least one part of a body.

7. The method according to claim 1 wherein the images are kinematic or static images of a position of the body or the at least one part of a body disposed in an imaging passage.

8. The method according to claim 1 wherein a predefined continuous movement of the body or the at least one part of a body or the support is generated or reproduced by the drive for the support.

9. The method according to claim 1 wherein the body or the at least one part of a body includes a joint of a living object.

10. The method according to claim 1 wherein the body or the at least one part of a body is an ankle joint.

11. An apparatus for generating a passive movement of a body or at least one part of a body of an object in a magnetic resonance tomograph comprising:
    a support for positioning the body or the at least one part of a body, which support can be moved into and disposed in an imaging passage of the magnetic resonance tomograph;
    a drive motor for providing a defined reproducible passive movement which can be moved into and disposed in the passage of the magnetic resonance tomograph;
    the support or the body or the at least one part of the body can be moved or rotated or swiveled or pivoted independently about two axes;
    components of the support and the drive motor are made from non-ferromagnetic materials; and
    a control unit configured for controlling the drive motor to produce during the defined reproducible passive movement a series of images continuously in real time while or during imaging with the magnetic resonance tomograph.

12. The apparatus according to claim 11 wherein the drive motor moves or rotates or swivels or pivots the support or the body or the at least one part of a body.

13. The apparatus according to claim 11 wherein the control unit and/or the tomograph is electrically grounded and shielded from magnetic flux.

14. The apparatus according to claim 11 wherein the control unit is disposed outside a zone around the magnetic resonance tomograph in which the magnetic flux density is $\geq 0.2$ Tesla.

15. The apparatus according to claim 11 wherein the control unit is provided with at least one sensor for detecting the position of the support.

16. The apparatus according to claim 11 wherein the control unit is connected with a drive of the support and with sensors via electrically grounded and shielded lines, wherein the electrically grounded and shielded lines are outside the passage of the magnetic resonance tomography and are provided with ferrites.

17. The apparatus according to claim 11 wherein the support or the body or the at least one part of a body can be moved or rotated or swiveled or pivoted about a first horizontal axis and about a second axis inclined with respect to vertical by about 35° in a horizontal plane and by about 18° in a sagittal plane.

18. The apparatus according to claim 11 comprising:
    means for fixing the body or the at least one part of a body on the support; and
    at least portions of the support can be moved relative to the means for fixing.

19. The apparatus according to claim 11 wherein the support can be moved in a manner selected from the group consisting of pneumatically or hydraulically, the move being relative to means for fixing the body or the at least one part of the body.

20. The apparatus according to claim 11 wherein the drive of the support is in communication with the magnetic resonance tomograph via the control unit, such that images are acquired by the magnetic resonance tomograph simultaneously with the generation of the passive movement of the body or the at least one part of a body.

21. A magnetic resonance tomograph comprising an apparatus for generating a passive movement of the body or the at least one part of a body of the object according to claim 11.

22. The method of claim 1 wherein the body or the at least one part of the body is a living object.

23. The apparatus of claim 11 wherein the body or the at least one part of the body is a living object.

24. The apparatus of claim 11 wherein the passive movement comprises applying pressure or movement or swiveling or rotating or pivoting to the body or the at least one part of a body.

25. The apparatus of claim 11 wherein the drive motor provides for movement or rotating or swiveling or pivoting the support or the body or the at least one part of a body about at least one axis.

26. The method of claim 1 wherein the drive provides for movement or rotation or swiveling or pivoting the support or the body or the at least one part of a body about at least one axis.

27. The apparatus of claim 11 wherein the drive motor is a piezo-electromotor.

28. The method of claim 1 wherein the drive is a piezo-electromotor.

29. The method of claim 26 wherein the movement or rotation or swiveling or pivoting is selected from the group consisting of continuous, constant, adjustable, step-by-step, variable, and a combination thereof.

30. The method of claim 1 wherein the passive movement comprises applying a load on the body or the at least one body art by moving or swiveling or pivoting or rotating.

31. The method of claim 1 wherein the passive movement imitates the movement of the body or the at least one body part of the body.

32. The apparatus of claim 11 wherein the support or the body or the at least one part of a body can be moved or rotated or swiveled or pivoted about a first horizontal axis in a horizontal plane and in a sagittal plane.

33. The method of claim 1 wherein the passive movement comprises applying pressure to the support to move or rotate or swivel or pivot the body or the at least one part of the body.

34. The method according to claim 1 wherein the passive movement comprises applying a weight load on the body or the at least one part of a body or the support.

35. The method according to claim 1 wherein the passive movement produce or reproduces stress on the body or the at least one part a body or the support.

36. The apparatus according to claim 11 wherein the passive movement produce or reproduces stress on the body or the at least one part a body or the support.

* * * * *